(12) United States Patent
Kavsak

(10) Patent No.: US 8,491,871 B2
(45) Date of Patent: Jul. 23, 2013

(54) METHOD FOR ASSESSING RISK OF HEART FAILURE

(75) Inventor: Peter Kavsak, Oakville (CA)

(73) Assignee: McMaster University, Hamilton, ON (CA)

( * ) Notice: Subject to any disclaimer, the term of this patent is extended or adjusted under 35 U.S.C. 154(b) by 291 days.

(21) Appl. No.: 12/818,744

(22) Filed: Jun. 18, 2010

(65) Prior Publication Data

US 2010/0255520 A1 Oct. 7, 2010

Related U.S. Application Data

(63) Continuation-in-part of application No. PCT/CA2008/002236, filed on Dec. 18, 2008.

(60) Provisional application No. 61/008,594, filed on Dec. 21, 2007.

(51) Int. Cl.
*A61K 49/00* (2006.01)

(52) U.S. Cl.
USPC .................................. 424/9.1; 424/9.2; 435/4

(58) Field of Classification Search
USPC ........................................ 424/9.1, 9.2; 435/4
See application file for complete search history.

(56) References Cited

U.S. PATENT DOCUMENTS

2006/0094056 A1 5/2006 Chappell et al.

FOREIGN PATENT DOCUMENTS

| EP | 08863936.4 | 2/2011 |
| WO | WO 2009/079773 | 7/2009 |

OTHER PUBLICATIONS

Gorelik et al. "Multiplexed immunobead-based cytokine profiling for early detection of ovarian cancer", Cancer Epidemiol Biomarkers Prev 2005, 14(4):981-987.*
Sachdeva et al. "Biochip array-based analysis of plasma cytokines in HIV patients with immunological and virological discordance", Scandinavian J of Immunology, 65:549-554.*
Tian Y, et al., "The variation of serum cytokines in stress and coronary heart diseases", Clinical Chemistry; vol. 52, No. 6 supplement S, Jun. 1, 2006, p. A139.
Guo G H, et al., "To detect serum cytokines 8-13 by using biochip technology", Clinical Chemistry; vol. 51, No. supplement 6, Jan. 1, 2005, p. A119.
Fitzgerald S Pete et al: "Simultaneous 8-13 analysis of circulating human cytokines using a high-sensitivity cytokine biochip array.", Journal of Proteome Research Jan. 2008, (Nov. 17, 2007), pp. 450-455.
Laframboise et al. Cardiac fibroblasts influence cardiomyocyte phenotype in vitro. Am J Physiol Cell Physiol 292: C1799-C1808, 2007.
James et al. Usefulness of Biomarkers for Predicting Long-Term Mortality in Patients With Diabetes Mellitus and Non-ST-Elevation Acute Coronary Syndromes (A GUSTO IV Substudy). Am J Cardiol 2006;97:167-172.
Iwamoto, et al. ErbB and HB-EGF Signaling in Heart Development and Function. Cell Stuct Funct. 2006; 31:1-14.
Malarstig, et al. Raised interleukin-10 is an indicator of poor outcome and enhanced systemic inflammation in patients with acute coronary syndrome. Heart 2008;94:724-729. doi:10.1136/hrt.2007.119271.
Kavsak, et al. Rick stratification for heart failure and death in an acute coronary syndrome population using inflammatory cytokines and N-terminal pro-brain natriuretic peptide. Clinical Chemistry, 2007, 53:12, 2112-2118.
Kavsak et al. 'Upstream Markers' provide for an early identification of patients at high risk for myocaridal necrosis and adverse outcomes. Clinical Chemistry, Acta. Jan. 2008, (Epub Oct. 3, 2007), 387:1-2, 133-138.
Birner et al. Head-to-head comparison of BNP and IL-6 as markers of clinical and experimental heart failure: superiority of BNP. Nov. 2007, 40:2, 89-97.

* cited by examiner

*Primary Examiner* — Bin Shen

(57) ABSTRACT

A method of determining risk of heart failure in a mammal is provided comprising the steps of measuring in a biological sample obtained from a mammal the level of each of IL-6, MCP-1, IL-10, VEGF, and EGF biomarkers in the sample, wherein a positive result of at least three of said biomarkers is indicative of a risk of heart failure in the mammal.

8 Claims, 6 Drawing Sheets

METHOD FOR ASSESSING RISK OF HEART FAILURE

CROSS-REFERENCE TO RELATED APPLICATIONS

This application is a CIP of PCT/CA2008/002236 filed Dec. 18, 2008 which claims prior from U.S. provisional application 61/008,594 on Dec. 21 2007.

FIELD OF THE INVENTION

The present invention relates to a prognostic method in the field of cardiology, and in particular, to a method of assessing the risk of heart failure or death in a mammal.

BACKGROUND OF THE INVENTION

Modestly elevated concentrations of C-Reactive Protein (CRP), a marker of inflammation, has been shown to be predictive of both short and long-term risks for heart failure (HF) and death but not acute myocardial infarction (AMI), in patients with acute coronary syndromes (ACS). A recent report has also indicated that elevated CRP concentrations are associated with new heart failure in non-ACS patients with stable coronary artery disease. CRP is an acute phase reactant, but its concentration takes time to increase during an acute event. Furthermore, elevations are not specific for vascular inflammation. Interleukin 6 (IL-6) is a pro-inflammatory cytokine which is thought to be the most important proximate stimulator for CRP and also stimulates activation of leuckocytes. Interleukin-8 (IL-8) and Monocyte Chemoattractant Protein-1 (MCP-1) are both chemokines which recruit neutrophils and monocytes, respectively, to the inflammatory process. Elevated IL-6 and MCP-1 concentrations have previously been reported to be independent predictors for death/HF in an ACS population; however, inflammation represents only one pathological process in this setting and additional biomarkers assessing cardiac fibrosis, remodeling, function and survival are important for complete risk stratification.

It would be desirable, thus, to develop an accurate method predictive of the risk of death/heart failure in a mammal.

SUMMARY OF THE INVENTION

It has now been found that IL-6, MCP-1, IL-10, VEGF, and EGF may collectively be used as biomarkers to identify mammals at risk of heart failure or death, wherein a change in the concentration of at least three of these biomarkers as compared with a median baseline is indicative of a pathological state.

Thus, in one aspect of the present invention, a method of determining risk of heart failure in a mammal is provided comprising determining in a biological sample obtained from the mammal the concentration of each of IL-6, MCP-1, IL-10, VEGF, and EGF biomarkers in the sample, wherein a positive result of at least three of said biomarkers is indicative of a risk of heart failure in the mammal.

In another aspect of the invention, a kit useful to determine risk of heart failure in a mammal is provided. The kit comprises a cytokine-specific reactant for each of IL-6, MCP-1, IL-10, VEGF, and EGF, wherein each of said reactants is associated with an indicator capable of yielding a detectable product that is indicative of the concentration of the cytokine in a biological sample.

In another aspect of the invention, a method to screen for compounds useful to treat a mammal at risk of heart failure is also provided herein. The method comprises administering to a mammal a candidate compound, and comparing the concentration levels of each of IL-6, MCP-1, IL-10, EGF and VEGF biomarkers in a biological sample obtained from the mammal before and after administration of the compound to the mammal. A determination that the compound modulates the concentration level of at least three of the biomarkers is indicative that the compound may be useful to treat a mammal at risk of heart failure/death.

In a further aspect of the invention, a method of monitoring the efficacy of a therapeutic compound or composition to treat a mammal at risk of heart failure/death is provided. The method comprises determining the levels of each of IL-6, MCP-1, IL-10, EGF and VEGF biomarkers in a biological sample obtained from the mammal prior to administration of the therapeutic compound and at one or more intervals subsequent to administration of the therapeutic compound to the mammal. A determination that the compound modulates the level of at least three of the biomarkers is indicative that the therapeutic compound may be effective to treat the mammal.

In another aspect of the invention, an article of manufacture useful to determine risk of heart failure in a mammal is provided comprising packaging and a cytokine-specific reactant for each of IL-6, MCP-1, IL-10, VEGF, and EGF, wherein each of said reactants is associated with an indicator capable of reacting to yield a detectable product that is indicative of the concentration of the cytokine in a biological sample obtained from a mammal, and wherein the packaging indicates that a positive result of at least three of said cytokines is indicative of a risk of heart failure in the mammal.

These, and other aspects of the invention, will become apparent from the following detailed description and figures which is briefly described below.

DETAILED DESCRIPTION OF INVENTION

Figure 1A:
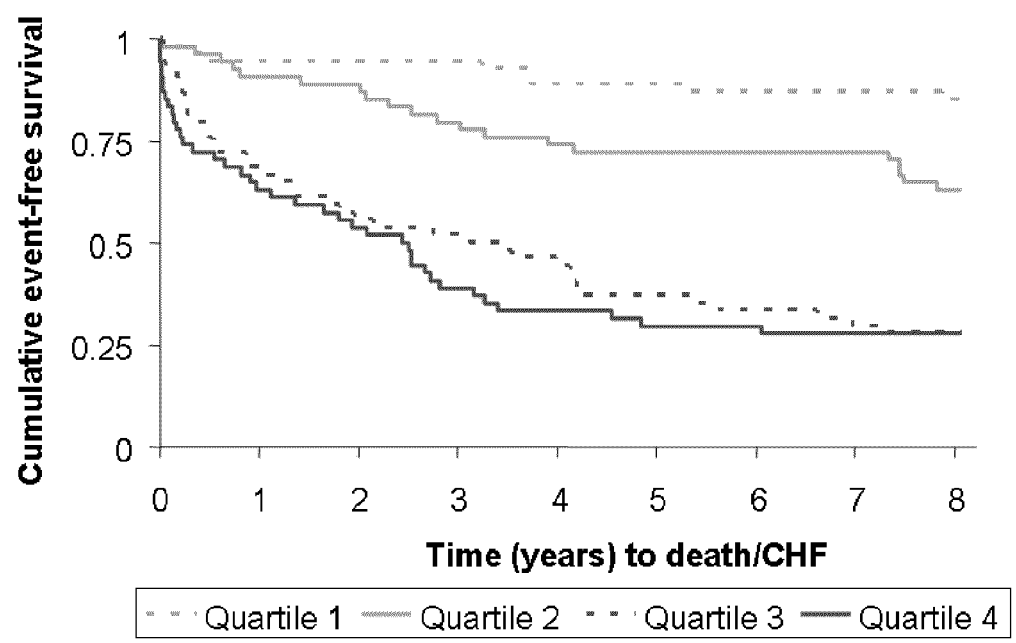
FIG. 1 illustrates Kaplan-Meier curves for cumulative event free survival (death/HF) for each of the biomarkers, IL-6 (A), VEGF (B), MCP-1 (C), IL-10 (D) and EGF (E) based on quartile analysis (Quartile 1 lowest concentration group and Quartile 4 highest concentration group)
Figure 1B:
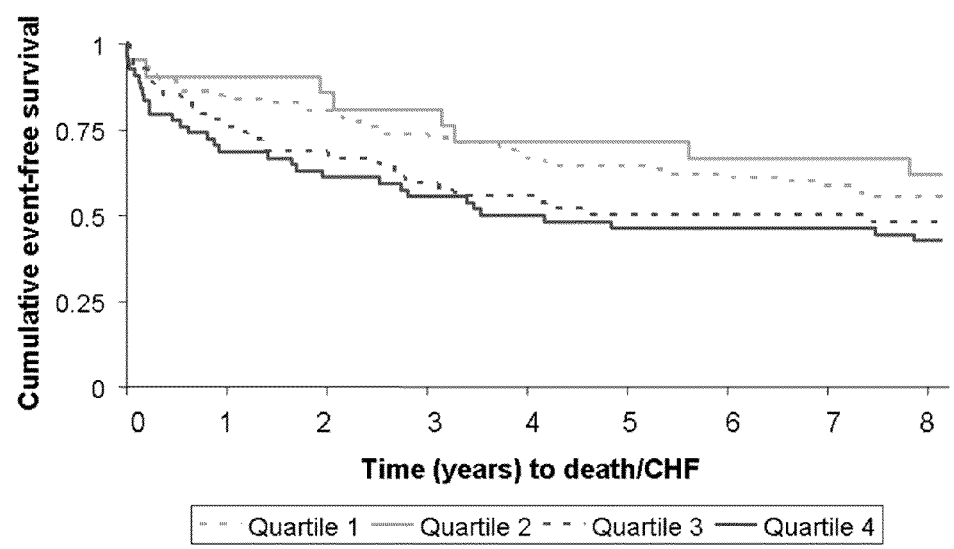
Figure 1C:
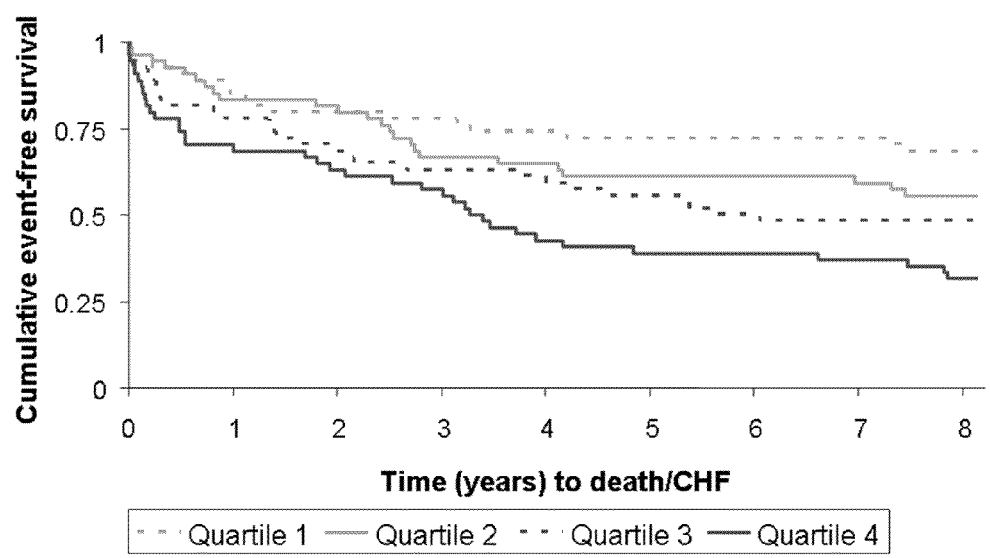
Figure 1D:
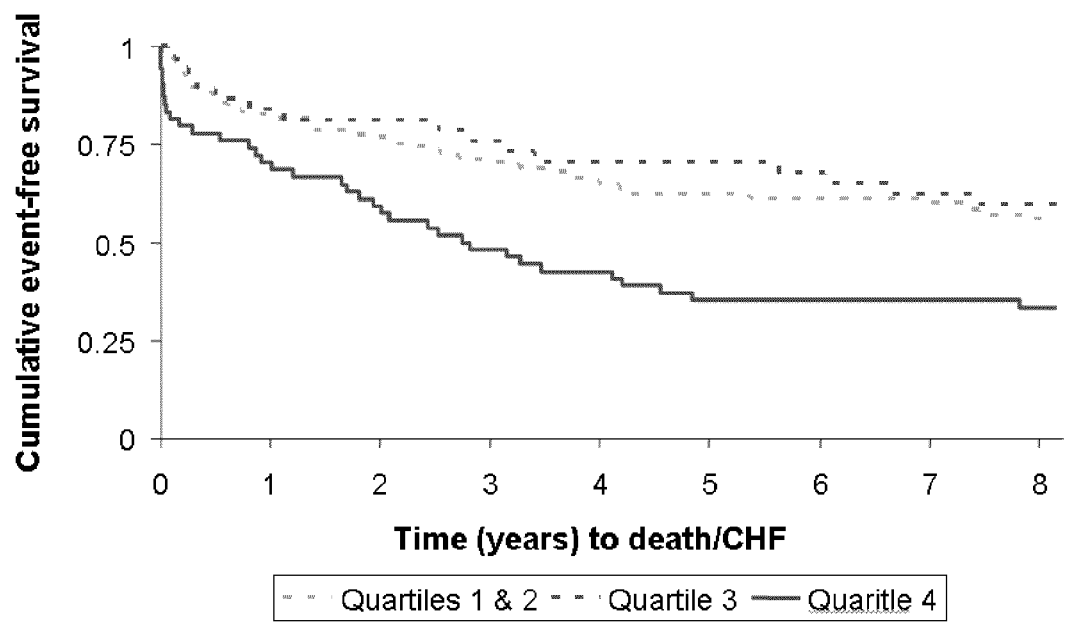
Figure 1E:
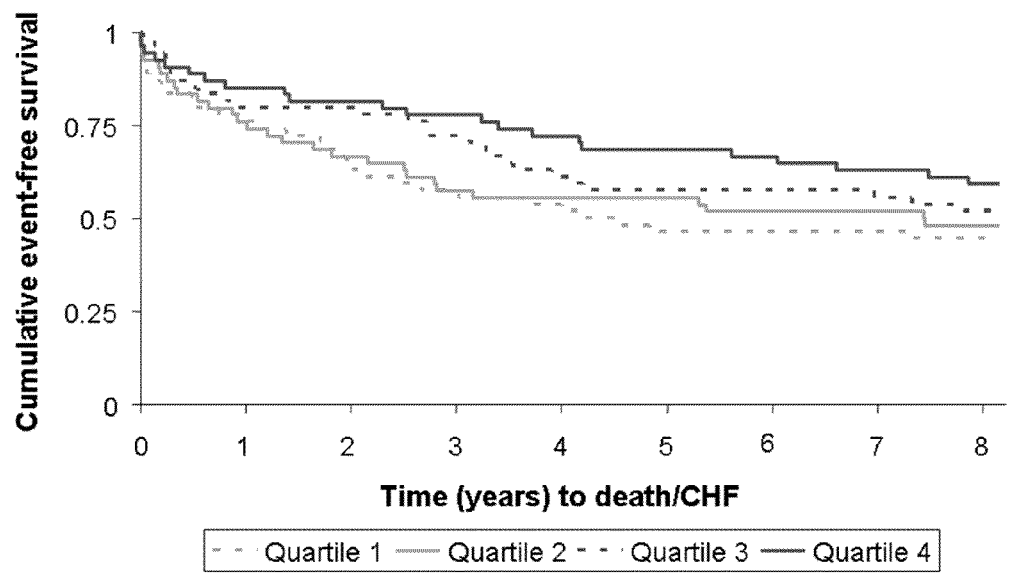

A method of determining risk of heart failure in a mammal is provided comprising the steps of measuring the level of each of IL-6, MCP-1, IL-10, VEGF, and EGF biomarkers in a biological sample obtained from the mammal. The determination of a positive result of at least three of these biomarkers is indicative of a risk of heart failure in the mammal.

The term "IL-6" refers to the mammalian cytokine, Interleukin-6, and encompasses both human IL-6, as depicted by NCBI accession no. NP000591, as well as IL-6 of other mammalian species, for example, mouse IL-6 as depicted NCBI accession no. NP112445. Also encompassed are IL-6-like compounds such as a gp130 cytokine family member (e.g. gp130, LIF-R (NP002301), OSM-R (Q99650), and G-CSF-R (NP000751), or a soluble gp130 receptor (e.g., soluble IL-6 receptor).

The term "MCP-1" refers to mammalian Monocyte Chemoattractant Protein-1 is a member of the small inducible gene (SIG) family and is also known as small inducible cytokine A2 (SCYA2) and monocyte chemotactic and activating factor (MCAF). "MCP-1" as used herein encompasses both human MCP-1, as depicted by NCBI accession no. NP000591, as well as MCP-1 of other mammalian species, for example, mouse MCP-1 as depicted by NCBI accession no. NP112445. Also encompassed are MCP-1-like compounds such as a compound of the CC chemokine family, e.g. CCL1-28, or a receptor thereof.

The term "IL-10" refers to mammalian Interleukin-10. IL-10 is also known as human cytokine synthesis inhibitory factor (CSIF) and is an anti-inflammatory cytokine. "IL-10" encompasses both human IL-10 as depicted by NCBI accession no. NP000563, as well as IL-10 of other mammalian species, for example, mouse IL-10 as depicted by NCBI accession no. NP034678. Also encompassed are IL-10-like compounds such as cytokines belonging to the extended IL-10 superfamily (e.g. the extended IL-10 superfamily: IL-10, IL-19, IL-20, IL-22, IL-24, IL-26, IL-28, and IL-29) or a receptor thereof.

The term "VEGF" refers to mammalian Vascular Endothelial Growth Factors of the platelet-derived growth factor family including VEGF-A, VEGF-B, VEGF-C and VEGF-D and splice variants $VEGF_{121}$, $VEGF_{121}b$, $VEGF_{145}$, $VEGF_{165}$, $VEGF_{165}b$, $VEGF_{189}$, $VEGF_{206}$. "VEGF" as defined encompasses both human VEGF, for example VEGF-A as depicted by NCBI Accession No. NP001020537 and VEGF-B as depicted by NCBI Accession No. XP001128909, and VEGF of other mammalian species, for example, mouse VEGF-A as depicted by NCBI Accession No. NP001020421 and mouse VEGF-B as depicted by NCBI Accession No. NP035827. Also encompassed are VEGF-like compounds belonging to the VEGF family such as P1GF (NP002634) and sVEGFR1 (or sFlt-1).

The term "EGF" refers to mammalian Epidermal Growth Factor (also known as beta-urogastrone), including human EGF, as depicted by NCBI Accession No. NP 001954, as well as EGF of other mammalian species, for example, mouse EGF as depicted by NCBI Accession No. NP 034243. Also encompassed are EGF-like compounds belonging to the EGF family such as HB-EGF (NP001936), sEGFR (NP005219) or soluble HER2 (NP001005862).

The term "mammal" is used herein to refer to both human and non-human mammals including domestic animals, e.g. cats, dogs and the like, livestock and undomesticated animals.

In a first step of the method, a biological sample is obtained from a mammal at risk for myocardial injury, e.g. mammals with acute coronary syndromes (ACS). The term "biological sample" is meant to encompass any mammalian sample that contains cytokine proteins such as IL-6, MCP-1, IL-10, VEGF, EGF and/or related proteins, e.g. related proteins, such as those described above, that may be indicative of the level or concentration of one of IL-6, MCP-1, IL-10, VEGF and EGF. Suitable biological samples include, for example, blood, serum, plasma and urine. The sample is obtained from the mammal in a manner well-established in the art.

Once a suitable biological sample is obtained, it is analyzed for the level of each of the cytokine proteins, IL-6, MCP-1, IL-10, EGF and VEGF. If necessary, or preferable, a related protein may be analyzed in place of any one of IL-6, MCP-1, IL-10, EGF and VEGF. This determination may be accomplished using various methods established in the art, for example, by Enzyme Linked ImmunoSorbent Assays (ELISAs) or Enzyme ImmunoAssay (EIA). In this assay, the cytokine to be analyzed is complexed with cytokine-specific reactant such as an antibody which is linked (either before or following formation of the complex) to an indicator, such as an enzyme. Detection may then be accomplished by incubating this enzyme-complex with a substrate, for example, that produces a detectable product. The indicator may be linked directly to the reactant (e.g. antibody) or via a linker, such as a secondary antibody that recognizes the first or primary antibody, or a protein such as streptavidin if the primary antibody is biotin labeled. Examples of suitable enzymes include, but are not limited to, horseradish peroxidase (HRP), alkaline phosphatase (AP), β-galactosidase, acetylcholinesterase and catalase. A large selection of substrates is available for performing the ELISA with an HRP or AP conjugate. Useful substrates depend on the level of detection required and the detection instrumentation used, e.g. spectrophotometer, fluorometer or luminometer.

A convenient method by which cytokine levels in a sample may be determined utilizes, for example, biochip array technology. Generally, biochip arrays provide a means to simultaneously determine the level of multiple cytokines in a sample. These arrays are based on ELISA principles of sandwich or competitive immunoassays and, thus, the biochip provides a reaction platform including cytokine-specific antibodies attached at pre-defined sites on the surface. An amount of biological sample in the range of about 80-120 μl is generally used to conduct this determination of cytokine levels utilizing the biochip.

A determination of a concentration of any one of IL-6, MCP-1, IL-10 and VEGF which is greater than the median concentration level of the population being assessed is a positive result which is indicative of risk of heart failure, while a determination of a concentration level of EGF which is less than the median concentration level of the same population is a positive result which is indicative of heart failure. The greater the concentration difference of the measured cytokines from the median concentration level in a given population (e.g. the higher the concentration of IL-6, MCP-1, IL-10 and VEGF, and the lower the concentration of EGF to the median), the greater the risk of heart failure/death. It will be understood by one of skill in the art that the median concentration level of these cytokines may vary from population to population, which could include a general population for screening or a more specific high risk population such as an ED chest pain population. Accordingly, the concentration of each cytokine that qualifies as a positive result is dependent on a given population and the median concentration level of each cytokine within that population. Minimally, any increase in VEGF, IL-6, IL-10, MCP-1 or decrease in EGF from the median concentration, in any 3 of the cytokines, is sufficient to give a positive result when a cutpoint (or dichotomous) approach is used. However, when the biomarkers are treated as continuous variables the combination of more than 3 biomarkers (see Tables 5 & 6) yield significantly higher risk for heart failure/death as compared to those with only 2 biomarkers measured.

The present method is particularly useful to determine the risk for heart failure in patients with chest pain, ACS patients, patients on cardiotoxic treatment (e.g., cancer patients receiving cardiotoxic drugs and/or radiation to chest), diabetic patients, patients with rheumatoid arthritis, patients with high blood pressure, obese patients, and patients over the age of 65.

In addition, the present method is useful to determine risk of heart failure in a mammal with cardiac contusion, or other trauma including surgery, ablation, pacing, etc.; congestive heart failure—acute and chronic; aortic dissection; aortic valve disease; hypertrophic cardiomyopathy; tachy- or bradyarrhythmias, or heart block; apical ballooning syndrome; rhabdomyolysis with cardiac injury; pulmonary embolism, sever pulmonary hypertension; renal failure; acute neurological disease, including stroke or subarachnoid haemorrhage;

infiltrative diseases, e.g. amyloidosis, haemochromatosis, sarcoidosis, and scleroderma; inflammatory diseases, e.g. myocarditis or myocardial extension of endo- /pericarditis; and burns, especially if affecting >30% of body surface area. It is also useful to determine risk of heart failure in mammals that are critically ill, especially with respiratory failure or sepsis, and mammals that have experienced extreme exertion.

A method to screen for compounds therapeutically useful to treat a mammal at risk of heart failure is also provided herein. The method comprises administering to a mammal a candidate compound, e.g. a potential therapeutic compound, and determining in a biological sample obtained from the mammal the levels of each of IL-6, MCP-1, IL-10, EGF and VEGF. A determination that the compound modulates the level or concentration of at least three of these cytokines favoring a lower risk of heart failure/death, e.g. a reduction in the levels of IL-6, MCP-1, IL-10 and VEGF, and an increase in the level of EGF (see FIG. 1 illustrating lower concentrations are favorable for IL-6, VEGF, MCP-1, IL-10 and higher concentrations are favourable for EGF), in comparison to the cytokine levels prior to administration of the candidate compound to the mammal is indicative that the candidate compound may be useful to treat a mammal at risk of heart failure/death.

As will be appreciated, depending on the combination of biomarkers that are determined to be positive, potentially useful therapeutic compounds may be identified which may decrease the level of some cytokines while increasing the level of other cytokines, but which may result in an overall favourable profile in a mammal. For example, in a mammal determined to have an increased level of IL-6, MCP-1 and VEGF and decreased level of IL-10 and EGF, a compound which desirably decreases IL-6, MCP-1, VEGF, but concomitantly increases IL-10 levels and decreases EGF, provides a treatment that results in an overall favourable profile for the mammal despite the increased IL-10 and decreased EGF levels.

A method of monitoring the efficacy of a therapeutic compound or composition to treat a mammal at risk of heart failure/death is also provided in another aspect of the invention. The method comprises determining the levels of each of IL-6, MCP-1, IL-10, EGF and VEGF in a biological sample obtained from the mammal prior to administration of the therapeutic compound and at one or more intervals subsequent to administration of the therapeutic to the mammal. A determination that the compound modulates the level of these cytokines favoring a lower risk of heart failure/death (see FIG. 1) in comparison to the cytokine levels prior to administration of the candidate compound to the mammal is indicative that the therapeutic compound may be effective to treat the mammal.

A kit useful to determine risk of heart failure in a mammal is provided in a further aspect of the invention. The kit comprises a cytokine-specific reactant for each of IL-6, MCP-1, IL-10, VEGF, and EGF (e.g. antibodies specific to each cytokine). Each of the reactants is associated with an indicator (e.g. an enzyme, such as horseradish peroxidase (HRP), alkaline phosphatase (AP), β-galactosidase, acetylcholinesterase and catalase) which is capable of yielding a detectable product that is indicative of the concentration of the cytokine in the biological sample, for example, by reacting with a substrate to produce a detectable product.

In accordance with the present method of determining risk of heart failure in a mammal, an article of manufacture is provided that is useful to conduct the method. The article of manufacture comprises instructions and cytokine-specific reactants for each of the cytokines IL-6, MCP-1, IL-10, VEGF, and EGF. Alternatively, a reactant to a closely related family member of any one of IL-6, MCP-1, IL-10, VEGF, and EGF, as described above, may be substituted for the IL-6, MCP-1, IL-10, VEGF, and EGF, respectively. Each of said reactants is associated with an indicator that is useful to determine the concentration of the cytokine to which the reactant binds. The instructions indicate that a positive result, as described above, of at least three of said cytokines is indicative of a risk of heart failure in the mammal.

Embodiments of the invention are described by reference to the following specific example which is not to be construed as limiting

EXAMPLE 1

Methods and Materials
Study Population

The study population and its characteristics have been previously reported in Kavsak et al. (Clin Chem. 2007; 53:2112-2118), the relevant contents of which are incorporated herein by reference.

At the time of study enrolment, 448 consecutive unique patients presenting to the emergency department in a community hospital with symptoms suggestive of cardiac ischemia were recruited for a retrospective cardiac marker study. Time of symptom onset was solicited and blood samples (both EDTA and heparin anti-coagulated blood from all patients) were collected at specified intervals (i.e., from time of symptom onset hourly until 6 h, and then at 9, 12, 24, and 48 h) until the patient was discharged, declined further participation, or was removed from the study by those responsible for his/her care. All specimens were frozen, predominately at −70° C. The heparin specimens were thawed and cardiac troponin I (cTnI) and CRP measurements were performed on the Access® (AccuTnI assay) and Image® (high sensitivity CRP assay) instruments, respectively, from Beckman Coulter Inc. The stability of Troponin I and CRP was previously confirmed in the cohort. For the present study, only those subjects were selected (n=216) who had at least two EDTA specimens available in storage. The median ($25^{th}$-$75^{th}$ percentile) number of specimens per subject was 3(2-5) and all specimens (n=723) were measured for IL-6, MCP-1, IL-10, VEGF, EGF and NT-proBNP to provide a serial and temporal profile of the biomarkers. For the outcome analysis, only 2 specimens per subject were selected based on the following criteria: the earliest available ($1^{st}$ specimen) and the next closest to 9 h post onset ($2^{nd}$ specimen). In the event that the $1^{st}$ specimen obtained was greater than 6 h post onset, then the next specimen at least 3 hours later was selected as the $2^{nd}$ specimen. Thus the minimum interval between specimen pairs was 3 h with the median ($25^{th}$-$75^{th}$) being 6.5 h (5-8).

Biomarker Measurements

The EDTA specimens were thawed and a cytokine array was measured using the evidence Investigator™ (Randox Ltd) biochip platform. The biochip can assay 12 cytokines, however, only IL-6, MCP-1, IL-10, VEGF and EGF were evaluated for the present study assessing the utility of these 5 biomarkers for predicting heart failure or death in a population at risk for myocardial injury (i.e., an ACS population). The interassay (n=20 assays) imprecision (CV), determined by measuring 3 levels of quality control material, ranged from 9.2-13.2% for IL-6, MCP-1, IL-10, VEGF, and EGF. The NT-proBNP was measured with the Elecsys® 1010 (Roche) with interassay impression <7%.

Panel Test Interpretation

The 5 biomarkers: IL-6, MCP-1, IL-10, VEGF and EGF may have different biological functions and perhaps different roles that may be synergistic and/or complementary to each other which enhance the risk for patients for subsequent death/HF. As such, the decision was made to score each biomarker as follows: if the concentration of IL-6 is >the median concentration then label this test as positive; if the concentration of IL-10 is >the median concentration then label this test as positive; if the concentration of VEGF is >the median concentration then label this test as positive; if the concentration of MCP-1 is >the median concentration then label this test as positive; if the concentration of EGF is <(less than) the median concentration then label this test as positive. After scoring each of the 5 biomarkers within the same sample (i.e., $2^{nd}$ sample-9 h post onset of pain), a new variable was created. The number of positive tests per subject was recorded (0-5 positive tests/subject). Those with 3 or more positive tests were compared to those with 0-2 positive tests for death/HF. In addition, another approach was employed that assessed the different individual contributions for each biomarker for predicting outcome, thus allowing one to determine if there was a synergistic relationship between the 5 biomarkers in the panel for predicting long-term death/HF as compared to models only including 2 biomarkers.

Health Outcomes and Statistical Analysis

Research ethics board approval was obtained to measure biomarkers in the stored samples and to make health outcome linkages to the Registered Persons Data Base (RPDB) for mortality outcomes and the Canadian Institute for Health Information Discharge Abstract Database (CIHI-DAD) for hospital discharges associated with HF. Both the RPDB and CIHI-DAD (i.e., administrative databases) have been reported to be highly accurate in obtaining these endpoints. Based on the death date and earliest subsequent readmission for HF, indicators were created to reflect whether or not an event (death or HF readmission) occurred within 8 years post presentation (patients who died without previous HF readmission or follow-up were censored at the date of death). The biomarker concentrations (e.g. IL-6, MCP-1, IL-10, VEGF, EGF) in the later (i.e. $2^{nd}$) specimen were used to determine the risk based on the hypothesis that this specimen would better reflect the severity of cardiomyocyte dysfunction and the inflammatory response of the patient than the earlier specimen. Of note, exploratory analyses using logistic regression models with the cytokines for the combined endpoint death/HF suggested no difference on long-term outcomes (e.g., at 8 years) between the $1^{st}$ and $2^{nd}$ specimen; however, the $2^{nd}$ specimen tended to be more predictive for early outcomes (e.g., 30 days and 1 year) as compared to the $1^{st}$ specimen (see Table 1).

TABLE 1

Logistic regression analysis for death/HF for biomarkers in the 1st specimen (Time1) and the 2nd specimen (Time2).

| Composite outcome (death/HF) | marker | AUC Time1 | Time 2 |
|---|---|---|---|
| 1 year | il6 | 0.735 | 0.759 |
| | il10 | 0.723 | 0.754 |
| | vegf | 0.758 | 0.763 |
| | mcp1 | 0.732 | 0.735 |
| | egf | 0.721 | 0.722 |
| 30 days | il6 | 0.67 | 0.727 |
| | il10 | 0.654 | 0.719 |
| | vegf | 0.645 | 0.646 |
| | mcp1 | 0.659 | 0.674 |
| | egf | 0.645 | 0.647 |

(Note: models were adjusted for age and sex)

Quartile analysis for each of biomarkers, univariantly, was performed via the Kaplan-Meirer method. Briefly, based on the death date and earliest subsequent re-admission for heart failure (HF), indicators were created to reflect whether or not an event (death or HF readmission) occurred within 8 years post presentation (patients who died without previous HF readmission or follow-up were censored at the date of death). The biomarker concentrations in the later (i.e. $2^{nd}$) specimen was used for the quartile analysis for IL-6, VEGF, MCP-1, IL-10 and EGF. When combining the biomarkers, the analyses were based on the following classifications: those subjects with 0-2 positive tests versus those with 3-5 positive tests. For this study population (n=216), the combined endpoint (death/HF) was used for all analyses to maximize the number of events. Kaplan-Meier curves were constructed to display time to an event (death/HF), with differences between groups assessed by the log rank test. The Cox proportional hazard model was used to compare time to an event for those with ≧3 positive tests (3-5 positive tests) versus those with <3 positive tests (0-2 positive tests). Different models were used to assess the risk associated with those with ≧3 positive tests: model 1 adjusts for age (continuous variable), sex, history of HF, whereas model 2 adjusts for age (continuous variable), sex, history of HF, NT-proBNP relative to median, and cTnI levels. Cox proportional hazard models were also used to assess the ability of combinations of IL-6, MCP-1, IL-10, VEGF and EGF and their interactions to predict death/HF. Models were constructed for IL-6 alone, IL-6 and MCP-1 (with and without interaction), IL-6 and EGF (with and without interaction), IL-6 and VEGF (with and without interaction), IL-6 and IL-10 (with and without interaction) and compared to models including all 5 biomarker combinations (with and without interactions). For each of these models the likelihood ratio as well as the significance of the association based on the Wald chi-square statistic (p<0.05) was performed. Between-group comparisons of central tendency were based on the Wilcoxon and Kruskal-Wallis tests. Analyses were performed using SAS version 9.1.3 and GraphPad Prism version 5.00.

Results

For the 216 subjects (61% male), the median age ($25^{th}$-$75^{th}$ percentile) was 66 years (53-76). At the time of study enrolment in 1996, 19.4% of the subjects were diagnosed with acute myocardial infarction based on WHO MONICA criteria (Kavsak et al. Clin Chem. 2007; 53:2115, the contents of which are incorporated herein by reference). Applying the ESC/ACC criteria retrospectively based on the peak cTnI concentrations resulted in 44.4% of subjects having a cTnI concentration >$99^{th}$ percentile (>0.04 ug/L) (Kavsak et al. Clin Chem. 2007; 53:2115, the contents of which are incorporated herein by reference). Increases in both NT-proBNP and IL-6 concentration have been previously reported in the $2^{nd}$ specimen; however in the present analysis, the concentrations of both VEGF and IL-10 were decreased in the $2^{nd}$ specimen (median 9 h post-onset) as compared to the $1^{st}$ specimen (median 2 h post-onset), with no change in EGF concentrations between the 2 timepoints (Table 2).

TABLE 2

Biochemical characteristics [i.e., median (25-$75^{th}$ percentile)] for specimen set$^a$

| Variable | $1^{st}$ specimen | $2^{nd}$ specimen | D-value |
|---|---|---|---|
| Time from onset, h | 2 (2-4) | 9 (9-9) | |
| IL-6 (ng/L) | 4.0 (1.8-11.5) | 6.4 (2.8-17.0) | <0.001 |
| MCP-1 (ng/L) | 150 (116-202) | 155 (114-203) | 0.102 |
| IL-10 (ng/L) | 0.0 (0.0-1.4) | 0.0 (0.0-1.1) | 0.006 |

TABLE 2-continued

Biochemical characteristics [i.e., median (25-75th percentile)] for specimen set[a]

| Variable | 1st specimen | 2nd specimen | D-value |
|---|---|---|---|
| VEGF (ng/L) | 24.2 (14.5-48.1) | 13.8 (0.0-33.8) | <0.001 |
| EGF (ng/L) | 5.9 (2.8-12.7) | 5.0 (2.3-12.2) | 0.311 |

[a]note: pairs of specimens were at least 3 h apart, maximum 12 h

Spearman correlation analysis between all 5 biomarkers in the 2nd specimen revealed that IL-6 was the marker with the most correlation, whereas EGF was the least. However, none of the biomarkers were strongly correlated (r<0.40) (Table 3) and Kaplan Meier curves indicated that higher concentrations (univariantly) for IL-6, VEGF, MCP-1 and IL-10 are indicative of greater probability of heart failure/death, whereas subjects with higher concentrations of EGF had fewer events (less probability) (FIG. 1).

TABLE 3

Spearman Correlation for the 5 markers in the 2nd specimen (i.e., 9 hours post pain onset, n = 216)

|  | IL6 | IL10 | VEGF | MCP1 | EGF |
|---|---|---|---|---|---|
| IL6 |  | 0.35 | 0.20 | 0.39 | −0.05 |
| IL10 | 0.35 |  | 0.12 | 0.16 | −0.03 |
| VEGF | 0.20 | 0.12 |  | 0.06 | 0.19 |
| MCP1 | 0.39 | 0.16 | 0.06 |  | 0.05 |
| EGF | −0.05 | −0.03 | 0.19 | 0.05 |  | p < 0.05

Additional analyses using a more sensitive cardiac troponin assay (i.e., high-sensitivity cTn), measuring in the ng/L range, also did not detect differences between the 3-5 positive group versus the <3 positive group (p=0.63 for the earliest hs-cTnI measurement between the groups and p=0.52 for the peak hs-cTnI measurement between the groups).

Figure 2:
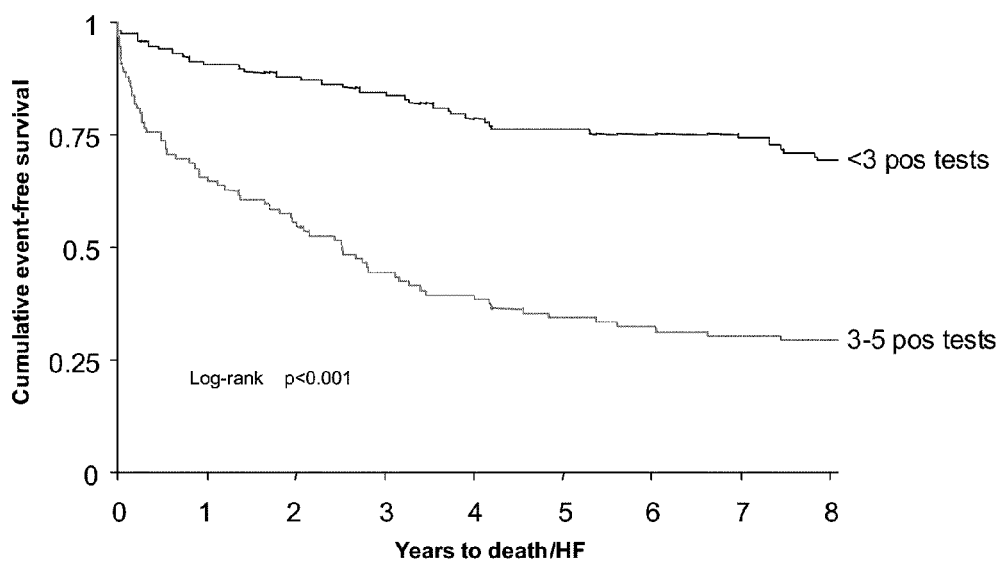
FIG. 2 illustrates Kaplan-Meier survival curves for a 3-5 positive biomarker group as compared to a <3 positive biomarker group.

Kaplan-Meier analysis assessing individuals with 3 or more positive tests versus those with less than 3 positive tests (i.e., 3-5 pos vs. <3 pos tests) in the later specimen (i.e. 2nd specimen) demonstrated that those with 3 or more positive tests had a greater probability for death/HF over the 8 years following the emergency department presentation (FIG. 2). Of note, there was no difference in cTnI and NT-proBNP concentrations between the 3-5 positive group versus the <3 positive group (p=0.091 and p=0.987, respectively) and the proportion of males versus females in the 3-5 positive group was also not different (44% vs. 49%, p=0.48).

Cox proportional hazard models adjusting for age, sex, and history of HF, yielded significant hazard ratios for the 3-5 positive group versus the <3 positive group at 6 months, 2 years and 8 years. Even after adjusting for NT-proBNP and cTnI concentrations in the analysis, the 3-5 positive group still had significant hazard ratios at all 3 timepoints (Table 4).

TABLE 4

Hazard Ratios for death/HF at 6 months, 2 years, 8 years. Cox proportional hazard models for the 3-5 positive group vs. the <3 positive group.

| Model | Time since presentation | HR relative to <3 pos tests | Lower 95% CL | Upper 95% CL | Chi-square p-value |
|---|---|---|---|---|---|
| 1 | 6 months | 3.755 | 1.585 | 8.896 | 0.003 |
|  | 2 years | 3.054 | 1.639 | 5.693 | <0.001 |
|  | 8 years | 2.729 | 1.795 | 4.148 | <0.001 |
| 2 | 6 months | 3.171 | 1.327 | 7.579 | 0.009 |
|  | 2 years | 2.581 | 1.371 | 4.858 | 0.003 |
|  | 8 years | 2.736 | 1.788 | 4.185 | <0.001 |

Model 1 adjust for age at presentation, sex, history of heart failure

Model 2 adjust for age at presentation, sex, history of heart failure, NT-proBNP relative to median, and cTnI levels.

To assess whether the combination of all 5 biomarkers (which represent a panel of biomarkers involved in inflammation, cardiac fibrosis and cardiomyocyte function) would yield a model that better predicted outcomes, the 5 biomarker panel was compared to different combinations of 2 biomarkers. As seen in Table 5, the 5 biomarker panel was a better predictor for death/HF as compared to the different 2 biomarker combination models.

TABLE 5

Cox proportional hazard models for assessing combinations of the 5 biomarkers vs. models with only 2 biomarkers for death/HF at 8 years.

| Model | Markers in model | Likelihood Ratio Chisq | Degrees of Freedom | Models compared | P-value for difference in Chisq |
|---|---|---|---|---|---|
| 1 | IL-6 only | 16.500 | 1 | Reference |  |
| 2 | IL-6, MCP-1 | 19.300 | 2 | 2 vs 1 | 0.094 |
| 3 | IL-6, EGF | 16.656 | 2 | 3 vs 1 | 0.693 |
| 4 | IL-6, VEGF | 21.781 | 2 | 4 vs 1 | 0.022 |
| 5 | IL-6, IL-10 | 21.134 | 2 | 5 vs 1 | 0.031 |
| 11 | IL-6, MCP-1, EGF, VEGF, IL-10 | 30.218 | 5 |  |  |
|  | difference in LR | 13.718 | 4 | 11 vs 1 | 0.005 < p < 0.010 |
|  | difference in LR | 10.918 | 3 | 11 vs 2 | 0.010 < p < 0.025 |
|  | difference in LR | 13.562 | 3 | 11 vs 3 | p < 0.005 |
|  | difference in LR | 8.437 | 3 | 11 vs 4 | 0.025p < 0.50 |
|  | difference in LR | 9.084 | 3 | 11 vs 5 | 0.025p < 0.050 |

(Note: the biomarkers were treated as continuous variables in the model, thus the Likelihood Ratio chi-square refers to how well the model predicts outcome so it doesn't matter which direction the association is. The p-values are associated with the difference in LR chi-squares between the models.)

Moreover, when assessing whether the interaction between the biomarkers significantly improved the model, 4 biomarkers demonstrate superiority to the 2 biomarker combinations (see Table 6). Therefore, all 5 biomarkers (or two 4 biomarker combinations including the interaction terms) yield models that are superior to the 2 biomarker combinations as evidenced by the higher likelihood ratios.

TABLE 6

Cox proportional hazard models to assess the combination and interaction of 4 biomarkers vs. models with only 2 biomarkers for death/HF at 8 years

| Model | Markers in model | Likelihood Ratio Chisq | Degrees of Freedom | Models compared | P-value for difference in Chisq |
|---|---|---|---|---|---|
| 2a | IL-6, MCP-1 + interxn | 22.684 | 3 | | |
| 3a | IL-6, EGF + interxn | 22.048 | 3 | | |
| 4a | IL-6, VEGF + interxn | 21.834 | 3 | | |
| 5a | IL-6, IL-10 + interxn | 21.545 | 3 | | |
| 9a | IL-6, MCP-1, EGF, VEGF + interxn | 48.183 | 15 | | |
| | difference in LR | 25.499 | 12 | 9a vs. 2a | 0.010 < p < 0.025 |
| | difference in LR | 26.135 | 12 | 9a vs. 3a | 0.010 < p < 0.025 |
| | difference in LR | 26.349 | 12 | 9a vs. 4a | 0.005 < p < 0.010 |
| 10a | IL-6, MCP-1, EGF, IL-10 + interxn | 49.249 | 15 | | |
| | difference in LR | 26.565 | 12 | 10a vs. 2a | 0.005 < p < 0.010 |
| | difference in LR | 27.201 | 12 | 10a vs. 3a | 0.005 < p < 0.010 |
| | difference in LR | 27.704 | 12 | 10a vs. 5a | 0.005 < p < 0.010 |

(Note: the biomarkers were treated as continuous variables in the model, thus the Likelihood Ratio chi-square refers to how well the model predicts outcome. The p-values are associated with the difference in LR chi-squares between the models.)

The present study confirms that IL-6, MCP-1, IL-10, VEGF and EGF are collectively effective as biomarkers in the determination of risk of heart failure in a patient. These biomarkers act synergistically to indicate an increased risk of heart failure in a patient such that a determination of a positive result of at least three of these biomarkers provides a greater than additive risk of heart failure as compared to a determination of only 2 biomarkers (e.g. at least 1.5× greater risk is indicated with a positive result of 4 of the biomarkers as compared to the risk associated with a positive result of only 2 biomarkers as shown in Table 6).

They were measured early after the onset of pain at a time when they have roles in the activation and recruitment of leukocytes during the inflammatory process, as well as effects on the process of fibrosis and myocyte function early in the injury process. Thus, the biological roles of the 5 biomarkers, together with their interplay, provides a biomarker panel that can be used in a time-dependent manner to provide a powerful tool for the identification of both men and women at risk for subsequent heart failure and death. All 5 biomarkers appear to have different and complementary functions during inflammation, cardiac fibrosis, and heart function, thus the panel provides an opportunity for a dose-dependent effect (i.e. graded effect) to be used in risk calculations for death/HF (e.g. 5 biomarkers are better than 2 biomarkers as shown in Table 5).

Thus, the use of the 5 biomarker panel early after the identification of cardiac injury or those at high risk of injury (either due to ischemic or non-ischemic causes) may identify those at greater risk for death/HF.

I claim:

1. A method of determining risk of heart failure in a mammal comprising;
    i) determining in a biological sample obtained from the mammal the concentration level of each of IL-6, MCP-1, IL-10, VEGF, and EGF biomarkers in the sample;
    ii) comparing the level of each biomarker in the sample to a median concentration of each of the biomarkers in a given population;
    iii) determining whether or not the level of each biomarker constitutes a positive result, wherein a positive result is represented by an increase in the concentration of any of IL-6, MCP-1, IL-10 and VEGF and a decrease in the concentration of EGF in the sample as compared with the median concentration; and
    iv) identifying the mammal as at risk of heart failure on determination of a positive result of at least three of said biomarkers in the sample.

2. The method as defined in claim 1, wherein the concentration of each biomarker is determined using a cytokine-specific reactant for each biomarker, wherein each of said reactants is associated with an indicator capable of yielding a detectable product that is indicative of the concentration of the cytokine in the biological sample.

3. The method as defined in claim 2, wherein the cytokine-specific reactant is an antibody.

4. The method as defined in claim 2, wherein the indicator is an enzyme capable of reacting with a substrate to yield a detectable product.

5. The method as defined in claim 1, wherein risk of heart failure in the mammal is identified by determining a positive result in at least 4 of said biomarkers.

6. The method as defined in claim 1, wherein the greater the positive result of one or more of said at least 3 biomarkers, the greater the risk of heart failure.

7. A method of screening or monitoring the efficacy of a candidate compound to treat a mammal at risk of heart failure comprising:
    1) determining the levels of each of IL-6, MCP-1, IL-10, EGF and VEGF biomarkers in a biological sample obtained from the mammal prior to administration of the compound;
    2) administering to the mammal the compound;
    3) determining the concentration levels of each of IL-6, MCP-1, IL-10, EGF and VEGF biomarkers at one or more intervals following administration of the compound to the mammal and
    4) assessing whether or not the candidate compound may be useful to treat a mammal at risk of heart failure, wherein a candidate compound is assessed as potentially useful to treat a mammal at risk of heart disease when it is determined that the candidate compound modulates the concentration level of at least three of the biomarkers following administration.

8. The method as defined in claim 7, wherein a determination that the compound modulates the concentration of at least three of the biomarkers by decreasing the concentration of IL-6, MCP-1, IL-10 and VEGF, and increasing the concentration of EGF.

* * * * *